US012629268B2

(12) United States Patent
Guo et al.

(10) Patent No.: US 12,629,268 B2
(45) Date of Patent: May 19, 2026

(54) BALLOON STENT MOUNTING DEVICE AND STENT MOUNTING METHOD

(71) Applicant: SUZHOU ZENITH VASCULAR SCITECH LIMITED, SIP Suzhou (CN)

(72) Inventors: Liyou Guo, SIP Suzhou (CN); Jie Xia, SIP Suzhou (CN)

(73) Assignee: SUZHOU ZENITH VASCULAR SCITECH LIMITED, Sip Suzhou (CN)

( * ) Notice: Subject to any disclaimer, the term of this patent is extended or adjusted under 35 U.S.C. 154(b) by 168 days.

(21) Appl. No.: 18/564,758

(22) PCT Filed: Jun. 8, 2022

(86) PCT No.: PCT/CN2022/097657
§ 371 (c)(1),
(2) Date: Nov. 28, 2023

(87) PCT Pub. No.: WO2023/024646
PCT Pub. Date: Mar. 2, 2023

(65) Prior Publication Data
US 2024/0252332 A1      Aug. 1, 2024

(30) Foreign Application Priority Data

Aug. 27, 2021    (CN) .......................... 202110992733.8

(51) Int. Cl.
*A61F 2/95*        (2013.01)
*A61F 2/958*       (2013.01)
(Continued)

(52) U.S. Cl.
CPC ............ *A61F 2/9522* (2020.05); *A61F 2/958* (2013.01); *A61M 29/02* (2013.01); *A61M 25/09* (2013.01);
(Continued)

(58) Field of Classification Search
CPC .. A61F 2/966; A61F 2/958; A61F 2/96; A61F 2/95; A61M 25/104; A61M 25/09
See application file for complete search history.

(56) References Cited

U.S. PATENT DOCUMENTS 4,079,738 A  *  3/1978  Dunn ................ A61M 25/0606
                                            604/164.05
4,314,555 A  *  2/1982  Sagae ............... A61M 39/0613
                                            604/168.01
(Continued)

FOREIGN PATENT DOCUMENTS

CN        2783951 Y      5/2006
CN        102274575 A    12/2011
(Continued)

OTHER PUBLICATIONS

International Search Report with English Translation and Written Opinion for PCT Application No. PCT/CN2022/097657, dated Sep. 15, 2022, 13 pages.
(Continued)

*Primary Examiner* — Andrew Restaino
(74) *Attorney, Agent, or Firm* — Dickinson Wright PLLC

(57)        ABSTRACT

Provided are a balloon stent mounting device and a stent mounting method. The balloon stent mounting device includes a balloon dilatation catheter and a stent release tube. The balloon dilatation catheter is provided with a first through hole along the length direction. A threading hole is disposed on the side wall of the first through hole. The micro guidewire enters the first through hole through the distal end of the balloon dilatation catheter and passes through the threading hole. An expansion part is disposed at a distal end of the balloon dilatation catheter. A self-expandable stent can be slidably mounted in the first through hole. The self-expandable stent is located at the distal end of the balloon dilatation catheter. The stent release tube is slidably
(Continued)

disposed in the first through hole of the balloon dilatation catheter. A distal end of the stent release tube abuts against the self-expandable stent.

14 Claims, 6 Drawing Sheets

(51) Int. Cl.
*A61M 25/09* (2006.01)
*A61M 29/02* (2006.01)

(52) U.S. Cl.
CPC ... *A61M 2029/025* (2013.01); *A61M 2210/12* (2013.01)

(56) References Cited

U.S. PATENT DOCUMENTS

| | | | | |
|---|---|---|---|---|
| 4,473,369 A * | 9/1984 | Lueders | A61M 39/1011 | |
| | | | 604/905 | |
| 4,493,708 A * | 1/1985 | Sugisawa | A61M 25/0606 | |
| | | | 604/44 | |
| 5,201,757 A | 4/1993 | Heyn et al. | | |
| 5,433,723 A * | 7/1995 | Lindenberg | A61F 2/95 | |
| | | | 606/198 | |
| 5,639,274 A | 6/1997 | Fischell et al. | | |
| 6,077,295 A * | 6/2000 | Limon | A61F 2/95 | |
| | | | 606/108 | |
| 8,758,421 B2 * | 6/2014 | Gerdts | A61F 2/966 | |
| | | | 606/191 | |
| 9,687,372 B2 * | 6/2017 | Dorn | A61F 2/966 | |
| 2005/0021125 A1 * | 1/2005 | Stack | A61F 2/95 | |
| | | | 623/1.11 | |
| 2008/0171979 A1 | 7/2008 | Brown et al. | | |
| 2008/0188804 A1 | 8/2008 | Jordan et al. | | |
| 2008/0269868 A1 | 10/2008 | Bei et al. | | |
| 2011/0028984 A1 * | 2/2011 | Jordan | A61M 25/00 | |
| | | | 606/108 | |
| 2013/0345787 A1 | 12/2013 | Igaki et al. | | |

FOREIGN PATENT DOCUMENTS

| | | | |
|---|---|---|---|
| CN | 102813995 A | | 12/2012 |
| CN | 202740600 U | * | 2/2013 |
| CN | 103479453 A | | 1/2014 |
| CN | 102813995 B | * | 3/2014 |
| CN | 209316785 U | | 8/2019 |
| CN | 111012557 A | | 4/2020 |
| CN | 210331338 U | | 4/2020 |
| CN | 210844903 U | | 6/2020 |
| CN | 211132632 U | | 7/2020 |
| CN | 113599037 A | | 11/2021 |
| CN | 215778935 U | | 2/2022 |
| EP | 0699451 A2 | | 3/1996 |

OTHER PUBLICATIONS

First Office Action for Chinese Application No. CN202110992733.8, dated Jun. 1, 2024, 10 pages.
English Translation of First Office Action for Chinese Application No. CN202110992733.8, dated Jun. 1, 2024, 9 pages.

* cited by examiner

BALLOON STENT MOUNTING DEVICE AND STENT MOUNTING METHOD

CROSS-REFERENCES TO RELATED APPLICATIONS

This application is a national stage application filed under 35 U.S.C. 371 based on International Patent Application No. PCT/CN2022/097657, filed on Jun. 8, 2022, which claims priority to Chinese Patent Application No. 202110992733.8 filed with the China National Intellectual Property Administration (CNIPA) on Aug. 27, 2021, the disclosures of which are incorporated herein by reference in their entireties.

TECHNICAL FIELD

The present application relates to the technical field of intravascular self-expandable stent delivery, for example, a balloon stent mounting device and a stent mounting method.

BACKGROUND

Vascular stenosis, a common vascular disease, is an important cause and risk factor for ischemic vascular disease. Vascular stent implantation is one of the important techniques to treat vascular stenosis.

During the operation of a related vascular stent implantation, a surgeon needs to first deliver a micro catheter and a microguidewire to the lesion, then remove the micro catheter, insert a balloon catheter to pre-expand the lesion, then withdraw the balloon catheter, inserts the micro catheter, and then, deliver the stent to the lesion through the microcatheter to release the stent and the stent is automatically stretched to dilate the blood vessel. In the preceding process, the micro catheter and the balloon catheter need to be alternately inserted into the blood vessel multiple times, which is prone to cause complications and increase operation time.

SUMMARY

Embodiments of the present application provide a balloon stent mounting device and a stent mounting method. With a balloon dilatation catheter mounted only once, a self-expandable stent can be delivered and mounted, so that a blood vessel can be dilated, operation steps can be reduced, the times of instruments exchanged in a patient's body and operation time can be reduced, and the success rate of the operation can be improved.

In an aspect, a balloon stent mounting device is provided, which is configured to mount a self-expandable stent to a lesion site of a blood vessel. The balloon stent mounting device includes a balloon dilatation catheter and a stent release tube.

The balloon dilatation catheter is provided with a first through hole along the length direction. A threading hole is disposed on the side wall of the first through hole. The balloon dilatation catheter is configured to enable a micro guidewire to enter the first through hole through a distal end of the balloon dilatation catheter and pass through the threading hole.

An expansion part is disposed at the distal end of the balloon dilatation catheter. The self-expandable stent is slidably mounted in the first through hole. The self-expandable stent is located at the distal end of the balloon dilatation catheter.

The stent release tube is slidably disposed in the first through hole of the balloon dilatation catheter. A distal end of the stent release tube abuts against the self-expandable stent.

In another aspect, a stent mounting method is provided, which uses the balloon stent mounting device described in any of the preceding schemes. The method includes the steps described below.

A compressed self-expandable stent is mounted to the distal end of the balloon dilatation catheter and the stent release tube is mounted in the first through hole.

The micro guidewire enters the first through hole through the distal end of the balloon dilatation catheter and passes through the threading hole.

The balloon dilatation catheter cooperates with the micro guidewire to push the expansion part of the balloon dilatation catheter to the lesion site.

The expansion part expands to stretch out the lesion site.

The expansion part contracts, and the balloon dilatation catheter is withdrawn until the stent release tube pushes the self-expandable stent out of the first through hole.

The balloon dilatation catheter and the stent release tube are withdrawn simultaneously.

BRIEF DESCRIPTION OF DRAWINGS

Drawings used in the description of embodiments of the present application are briefly described below.

Figure 1:
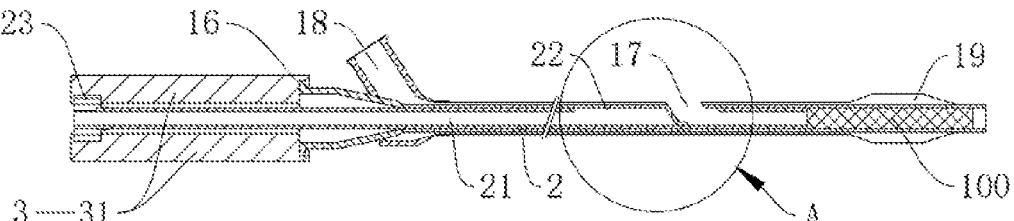
FIG. 1 is a sectional view of a balloon stent mounting device according to embodiment one of the present application.

Reference numbers of the drawings are listed as follows:
  100 self-expandable stent
  200 lesion site
  1 balloon dilatation catheter
  11 first through hole
  12 inlet
  13 outlet
  14 first guide wall
  15 second guide wall
  16 first handle
  17 threading hole
  18 fluid channel
  19 expansion part 191 expansion membrane
2 stent release tube
21 second through hole
22 avoidance notch
23 second handle
3 stopper assembly
31 stopper block
4 micro guidewire

DETAILED DESCRIPTION

Hereinafter the present application is described in conjunction with drawings and embodiments. It is to be understood that the embodiments set forth below are merely intended to illustrate the present application. It is to be further noted that for convenience of description, only some but not all structures related to the present application are shown in the accompanying drawings.

In the description of the present application, terms "connected to each other", "connected", or "secured" is to be construed in a broad sense, for example, as securely connected, detachably connected integrated; mechanically connected or electrically connected; directly connected to each other or indirectly connected to each other via an intermediary; or internally connected between two elements or interaction relations between two elements. For those of ordinary skill in the art, meanings of the preceding terms in the present application can be understood according to actual situations.

In the present application, when a first feature is described as "above" or "below" a second feature, the first feature and the second feature may be in direct contact or be in contact via another feature between the two features instead of being in direct contact. Moreover, when the first feature is "on", "above", or "over" the second feature, the first feature is right on, above, or over the second feature, or the first feature is obliquely on, above, or over the second feature, or the first feature is simply at a higher level than the second feature. When the first feature is "under", "below", or "underneath" the second feature, the first feature is right under, below, or underneath the second feature, or the first feature is obliquely under, below, or underneath the second feature, or the first feature is simply at a lower level than the second feature.

In the description of the embodiments, orientations or position relations indicated by terms such as "above", "below", "left", and "right" are based on the drawings. These orientations or position relations are intended only to facilitate the description and simplify an operation and not to indicate or imply that a device or element referred to must have such particular orientations or must be configured or operated in such particular orientations. In addition, terms "first" and "second" are used only to distinguish between descriptions and have no special meaning.

Embodiment One

During the operation of a related vascular stent implantation, a surgeon needs to first deliver a micro catheter and a microguidewire to the lesion, then remove the micro catheter, insert a balloon catheter to pre-expand the lesion, then withdraw the balloon catheter, inserts the micro catheter, and then, deliver the stent through the microcatheter to the lesion to release the stent and the stent is automatically stretched to dilate the blood vessel. In the preceding process, the micro catheter and the balloon catheter need to be alternately inserted into the blood vessel multiple times, which is prone to cause complications and increase operation time.

To solve the preceding problems, this embodiment provides a balloon stent mounting device (for example, a quick-exchange balloon stent mounting device), as shown in FIGS. 1 to 5. The balloon stent mounting device includes a balloon dilatation catheter 1 and a stent release tube 2. It is to be noted that in this embodiment, a "proximal end" refers to an end close to an operator, and a "distal end" refers to an end away from the operator and close to a lesion site 200.

Alternatively, as shown in FIGS. 1 to 3 and FIG. 9, the balloon dilatation catheter 1 is provided with a first through hole 11 along the length direction. A threading hole 17 is disposed on the side wall of the first through hole 11. A micro guidewire 4 can enter the first through hole 11 through a distal end of the balloon dilatation catheter 1 and pass through the threading hole 17. An expansion part 19 is disposed at the distal end of the balloon dilatation catheter 1. A self-expandable stent 100 is slidably mounted in the first through hole 11. The self-expandable stent 100 is located at the distal end of the balloon dilatation catheter 1. The stent release tube 2 is slidably disposed in the first through hole 11 of the balloon dilatation catheter 1. A distal end of the stent release tube 2 abuts against the self-expandable stent 100.

In this embodiment, in mounting the stent, a compressed self-expandable stent 100 can be mounted to the distal end of the balloon dilatation catheter 1, and the stent release tube 2 can be mounted in the first through hole 11. The micro guidewire 4 enters the first through hole 11 through the distal end of the balloon dilatation catheter 1 and passes through the threading hole 17. The balloon dilatation catheter 1 cooperates with the micro guidewire 4 to push the expansion part 19 of the balloon dilatation catheter 1 to the lesion site 200. Positive pressure is applied to the expansion part 19 to stretch out the lesion site 200. Negative pressure is applied to the expansion part 19, and the balloon dilatation catheter 1 is withdrawn. When the balloon dilatation catheter 1 is being withdrawn, the stent release tube 2 slides within the first through hole 11 relative to the balloon dilatation catheter 1 until the stent release tube 2 pushes the self-expandable stent 100 out of the first through hole 11. The self-expandable stent 100, after detached from the first through hole 11, automatically expands to dilate the blood vessel. While the self-expandable stent 100 automatically expands after detached from the first through hole 11, the balloon dilatation catheter 1 and the stent release tube 2 are withdrawn to complete the delivery and mounting of the self-expandable stent 100. In this embodiment, with a balloon dilatation catheter 1 mounted only once, a self-expandable stent 100 can be delivered and mounted, so that a blood vessel can be dilated, operation steps are reduced, the times of instruments exchanged in a patient's body and operation time can be reduced, and the success rate of the operation can be improved.

Alternatively, an inlet 12 is disposed at a proximal end of the balloon dilatation catheter 1. An outlet 13 is disposed at the distal end of the balloon dilatation catheter 1. The stent release tube 2 is configured to penetrate the first through hole 11 of the balloon dilatation catheter 1 through the inlet 12 of the balloon dilatation catheter 1.

Alternatively, the side wall of the stent release tube 2 is provided with an avoidance notch 22 matching the position of the threading hole 17. The length of the avoidance notch 22 is greater than that of the self-expandable stent 100. The avoidance notch 22 is configured to avoid the micro guidewire 4. The stent release tube 2 is provided with a second through hole 21 along the length direction. The micro guidewire 4 penetrates the outlet 13 of the first through hole 11, the self-expandable stent 100, the second through hole 21, and the avoidance notch 22 in sequence, and passes through the threading hole 17 to realize the guidance of the micro guidewire 4 to the balloon dilatation catheter 1. In this embodiment, when the balloon dilatation catheter 1 is withdrawn, the stent release tube 2 slides relative to the balloon dilatation catheter 1 to push out the self-expandable stent 100. Alternatively, to prevent the side wall of the stent release tube 2 from interfering with the micro guidewire 4, the length of the avoidance notch 22 can be configured to be greater than that of the self-expandable stent 100. In this manner, it is ensured that the side wall of the stent release tube 2 does not touch the micro guidewire 4 when the stent release tube 2 pushes out the stent.

Figure 2:
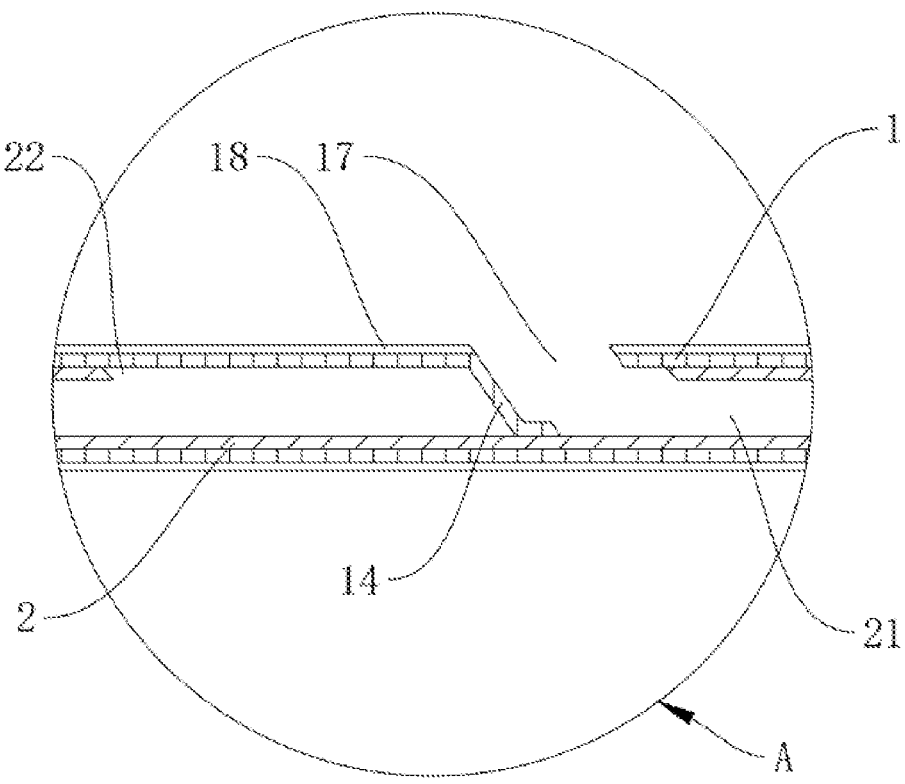
FIG. 2 is a partially enlarged view of part A of FIG. 1.
Figure 3:
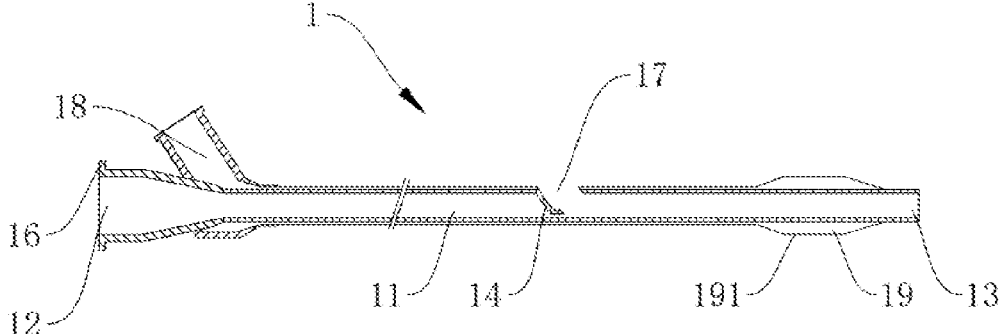
FIG. 3 is a sectional view of a balloon dilatation catheter according to embodiment one of the present application.

Alternatively, as shown in FIGS. 1 to 3, a first guide wall 14 is disposed on the side of the threading hole 17 away from the self-expandable stent 100. The first guide wall 14 is configured to provide guidance for the micro guidewire 4. The side wall of the stent release tube 2 is provided with an avoidance notch 22 matching the position of the threading hole 17. The length of the avoidance notch 22 is greater than that of the self-expandable stent 100. The avoidance notch 22 is configured to avoid the first guide wall 14 and the micro guidewire 4. In this embodiment, the first guide wall 14 and the balloon dilatation catheter 1 adopt flexible materials. An end of the first guide wall 14 can be flexibly disposed on the threading hole 17. When the stent release tube 2 is mounted, the stent release tube 2 enters the first through hole 11 through the inlet 12 of the balloon dilatation catheter 1. When the stent release tube 2 passes through the threading hole 17, the first guide wall 14 can be deformed in a direction away from the first through hole 11 so that the stent release tube 2 can continue to move towards the distal end of the balloon dilatation catheter 1. After the stent release tube 2 is mounted, the first guide wall 14 automatically rebounds and is inward recessed to abut against the inner wall of the second through hole 21. An end of the first guide wall 14 away from the threading hole 17 is inclined toward the direction close to the self-expandable stent 100. When assembled, the micro guidewire 4 can enter the first through hole 11 through the outlet 13. When the micro guidewire 4 passes through the threading hole 17, the first guide wall 14 provides guidance for the micro guidewire 4 to prevent the micro guidewire 4 from moving to a proximal side of the second through hole 21 after the micro guidewire 4 enters through the threading hole 17 to ensure that the micro guidewire 4 is delivered in the right direction.

Figure 4:
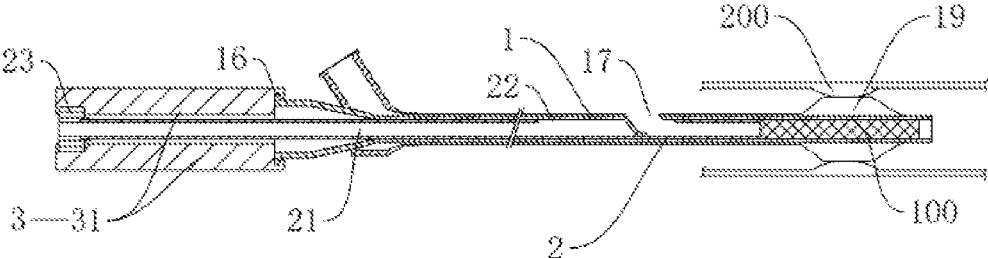
FIG. 4 is a sectional view of mounting a self-expandable stent in a first state according to embodiment one of the present application.
Figure 5:
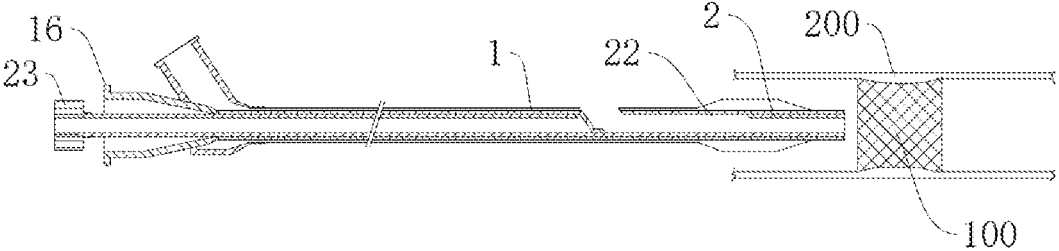
FIG. 5 is a sectional view of mounting a self-expandable stent in a second state according to embodiment one of the present application.

Alternatively, as shown in FIG. 1, FIG. 4, and FIG. 5 in this embodiment, the balloon stent mounting device also includes a stopper assembly 3, a first handle 16 is disposed at a proximal end of the balloon dilatation catheter 1, and a second handle 23 is disposed at a proximal end of the stent release tube 2. The stopper assembly 3 is provided with two card slots spaced apart. A cavity is disposed between the two card slots. The stopper assembly 3 is detachably mounted on the first handle 16 and the second handle 23 through the two card slots. A part of the side wall of the stent release tube 2 is located in the cavity. The distance between the two card slots is no less than the length of the self-expandable stent 100. The stopper assembly 3 is mounted on the first handle 16 and the second handle 23 to ensure that the balloon dilatation catheter 1 and the stent release tube 2 remain relatively stationary during the entry of the balloon dilatation catheter 1 into a blood vessel, preventing the stent release tube 2 from sliding relative to the balloon dilatation catheter 1 so as to avoid pushing out of the self-expandable stent 100 in advance. When the expansion part 19 of the balloon dilatation catheter 1 reaches the lesion site 200, the stopper assembly 3 is disassembled, and then the balloon dilatation catheter 1 is withdrawn. Since the stent release tube 2 remains stationary, the stent release tube 2 can push out the self-expandable stent 100. The distance between the two card slots is no less than the length of the self-expandable stent 100. The advantages of the configuration is to prevent the relative sliding distance between the stent release tube 2 and the balloon dilatation catheter 1 from being insufficient so as to completely push out the self-expandable stent 100.

Alternatively, the stopper assembly 3 includes two stopper blocks 31 that can be spliced. Grooves 33 are disposed on The side wall of each of the two stopper blocks 31 is respectively provided with a groove 33, the groove 33 on one of the two stopper blocks 31 is opposite to the groove 33 on another of the two stopper blocks 31. After the two stopper blocks 31 are spliced, opposite grooves are spliced to form the two card slots 32 and the cavity. The two stopper blocks 31 are assembled in a spliced manner. The first handle 16 and the second handle 23 provide positioning for the assembly of the two stopper blocks 31. The stopper assembly 3 is good in simple operation, easy disassembly and assembly, and strong practicability.

In an embodiment, alternatively, the side wall of the balloon dilatation catheter 1 includes an inner wall and an outer wall, a fluid channel 18 is disposed between the inner wall and the outer wall. The expansion part 19 is an expansion membrane 191 connected to the outer wall. A proximal end of the fluid channel 18 is connected to a fluid source. A distal end of the fluid channel 18 communicates with the expansion membrane 191. When the fluid source releases fluid, the fluid in the expansion membrane 191 increases to generate positive pressure, and the expansion membrane 191 expands outward to stretch out the lesion site 200. When the fluid source recovers the fluid, the fluid in the expansion membrane 191 decreases to generate negative pressure, and the expansion membrane 191 retracts to facilitate withdrawal of the balloon dilatation catheter 1. In this embodiment, the fluid released by the fluid source may be a liquid. In other embodiments, fluid may also be a gas.

In an embodiment, to facilitate an operator to obtain the position of the distal end of the balloon dilatation catheter 1 and the position of the self-expandable stent 100 in the blood vessel, a developing ring or a developing winding is mounted at the distal end of the balloon dilatation catheter 1 and a developing ring or a developing winding is also mounted on the outside of the self-expandable stent 100. Under radiation, the position of the distal end of the balloon dilatation catheter 1 can be obtained via an instrument, and the position and state of the self-expandable stent 100 can be detected via the instrument. The developing ring may be fixed by bonding. The developing winding may be fixed by winding.

Figure 10:
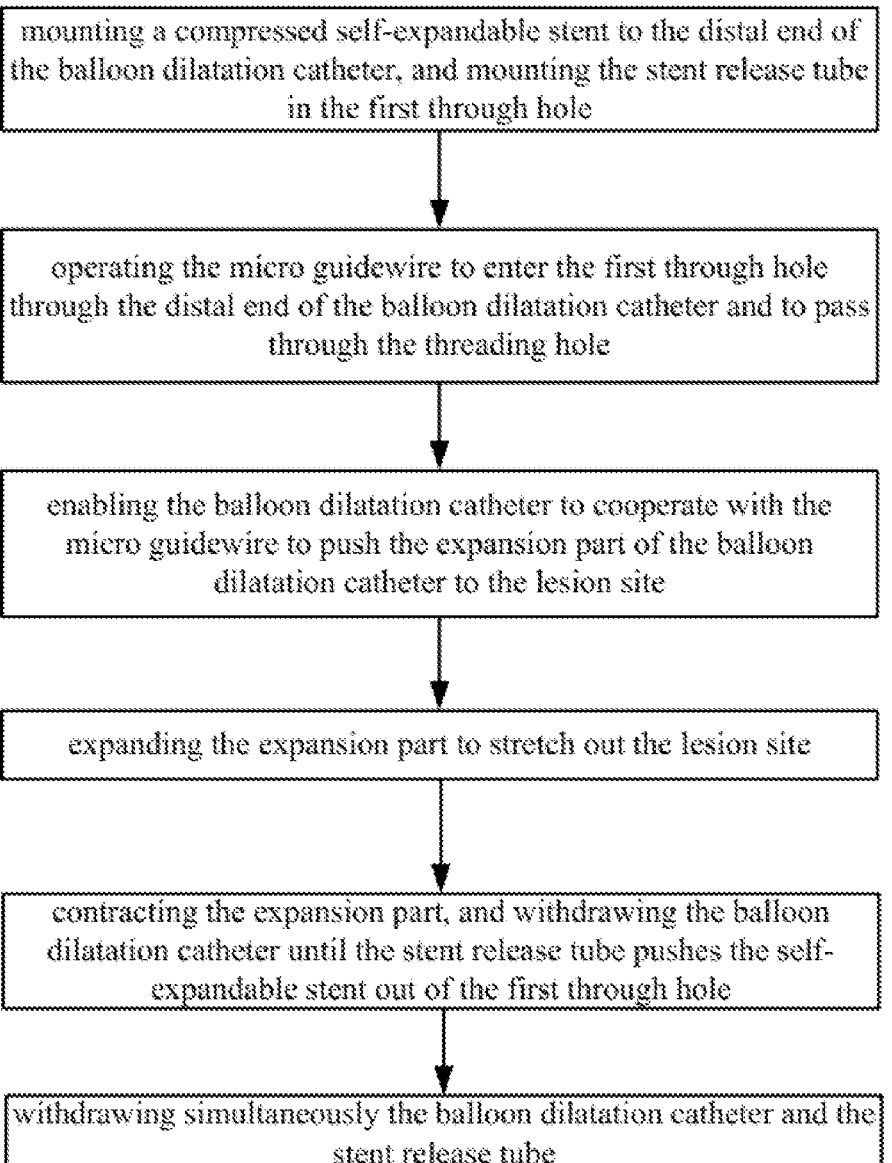
FIG. 10 is a flow chart of stent mounting method using the balloon stent mounting device according to the present application.

As shown in FIG. 10, this embodiment also provides a stent mounting method including the steps described below.

Step 1: A compressed self-expandable stent 100 is mounted to the distal end of the balloon dilatation catheter 1, and the stent release tube 2 is mounted in the first through hole 11.

Step 2: The micro guidewire 4 enters the first through hole 11 through the distal end of the balloon dilatation catheter 1 and passes through the threading hole 17.

Step 3: The balloon dilatation catheter 1 cooperates with the micro guidewire 4 to push the expansion part 19 of the balloon dilatation catheter 1 to the lesion site 200.

Step 4: The expansion part 19 expands to stretch out the lesion site 200.

Step 5: After the expansion part 19 contracts, the balloon dilatation catheter 1 is withdrawn until the stent release tube 2 pushes the self-expandable stent 100 out of the first through hole 11.

Step 6: The balloon dilatation catheter 1 and the stent release tube 2 are withdrawn simultaneously to complete the mounting operation of the self-expandable stent 100.

Alternatively, when the stopper assembly 3 is used, in step 2, the stopper assembly 3 is mounted on the first handle 16 and the second handle 23 after the stent release tube 2 is mounted in the first through hole 11 to improve the stability of the delivery of the balloon dilatation catheter 1. In step 5, after the expansion part 19 retracts, the stopper assembly 3 is removed.

In this embodiment, in mounting the stent, a compressed self-expandable stent can be mounted to the distal end of the balloon dilatation catheter, and the stent release tube is mounted in the first through hole. The micro guidewire 4 enters the first through hole through the distal end of the balloon dilatation catheter and passes through the threading hole. The balloon dilatation catheter cooperates with the micro guidewire 4 to push the expansion part of the balloon dilatation catheter to the lesion site. Positive pressure is applied to the expansion part to stretch out the lesion site. Negative pressure is applied to the expansion part, and the balloon dilatation catheter is withdrawn. When withdrawing the balloon dilatation catheter, the stent release tube slides within the first through hole relative to the balloon dilatation catheter until the stent release tube pushes the self-expandable stent out of the first through hole. The self-expandable stent, after detached from the first through hole, automatically expands to dilate the blood vessel. While the self-expandable stent 100 automatically expands after detached from the first through hole 11, the balloon dilatation catheter and the stent release tube are withdrawn to complete the delivery and mounting of the self-expandable stent. In this embodiment of the present application, with a balloon dilatation catheter mounted only once, a self-expandable stent can be delivered and mounted, so that a blood vessel can be dilated, the operation steps are reduced, the times of instruments exchanged in a patient's body and the operation time can be reduced, and the success rate of the operation can be improved.

Embodiment Two

Figure 6:
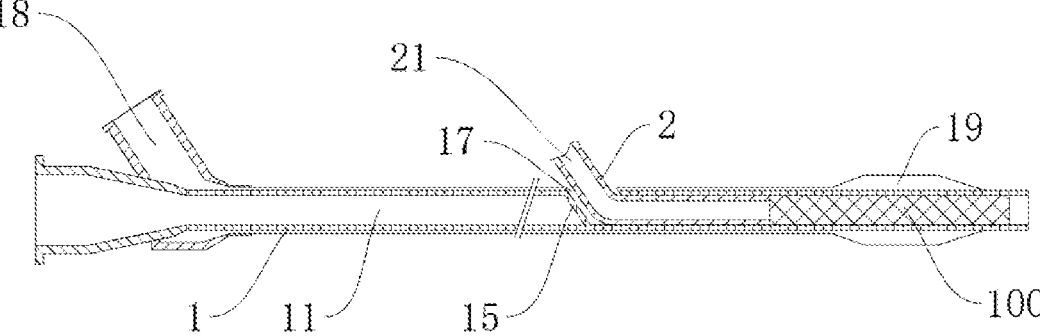
FIG. 6 is a sectional view of a balloon stent mounting device according to embodiment two of the present application.
Figure 7:
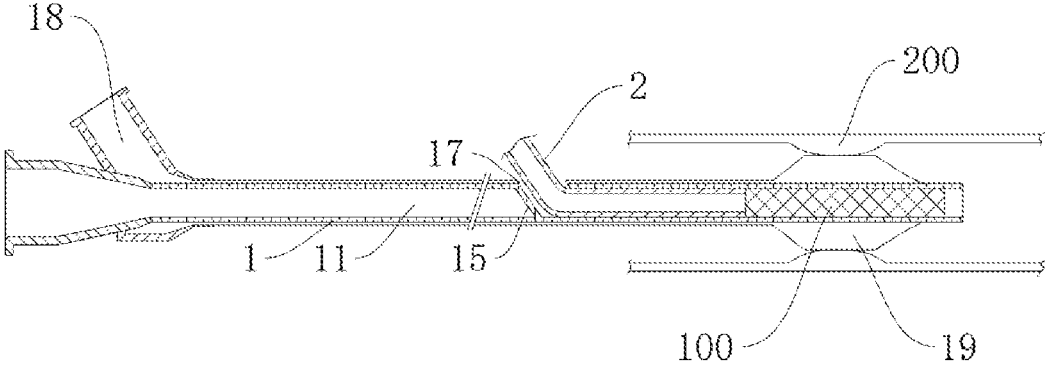
FIG. 7 is a sectional view of mounting a self-expandable stent in a first state according to embodiment two of the present application.
Figure 8:
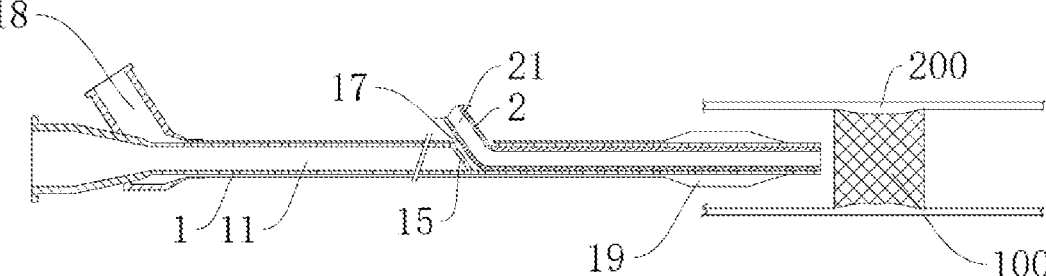
FIG. 8 is a sectional view of mounting a self-expandable stent in a second state according to embodiment two of the present application.
Figure 9:
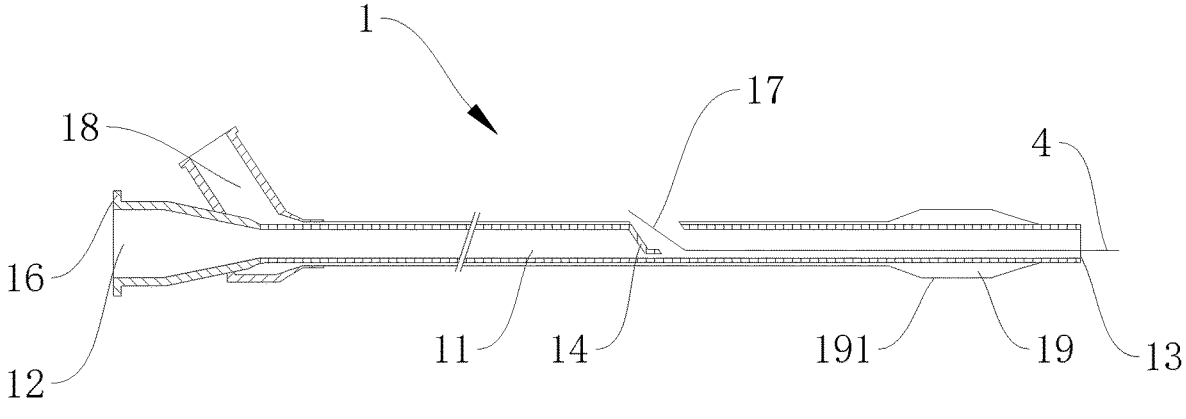
FIG. 9 is a sectional view of a balloon dilatation catheter according to embodiment one of the present application.

This embodiment also provides a balloon stent mounting device. The difference between this embodiment and embodiment one is that the mounting method of the stent release tube 2 is different from that of embodiment one, as shown in FIGS. 6 to 8. In this embodiment, the stent release tube 2 penetrates the first through hole 11 of the balloon dilatation catheter 1 through the threading hole 17, and the stopper assembly 3 of embodiment one is not included. In this embodiment, the first guide wall 14 of the balloon dilatation catheter 1 in embodiment one is replaced with a second guide wall 15 arranged obliquely. A part of the side wall of the second guide wall 15 is fixed to the side wall of the through hole 11. The side wall of the second guide wall 15 close to a side of the threading hole 17 is fixed to the threading hole 17. An end of the second guide wall 15 away from the threading hole 17 is inclined toward the direction close to the self-expandable stent 100.

In mounting the stent, a compressed self-expandable stent 100 can be mounted to the distal end of the balloon dilatation catheter 1. The micro guidewire 4 enters the first through hole 11 through the distal end of the balloon dilatation catheter 1 and passes through the threading hole 17. The balloon dilatation catheter 1 cooperates with the micro guidewire 4 to push the expansion part 19 of the balloon dilatation catheter 1 to the lesion site 200. Positive pressure is applied to the expansion part 19 to stretch out the lesion site 200. Negative pressure is applied to the expansion part 19 to make the expansion part contract. The stent release tube 2 enters the first through hole 11 through the threading hole 17 by using the micro guidewire 4 until the distal end of the stent release tube 2 abuts against the self-expandable stent 100, and the balloon dilatation catheter 1 is withdrawn. When withdrawing the balloon dilatation catheter 1, the stent release tube 2 slides within the first through hole 11 relative to the balloon dilatation catheter 1 until the stent release tube 2 pushes the self-expandable stent 100 out of the first through hole 11. The self-expandable stent 100, after detached from the first through hole 11, automatically expands to dilate the blood vessel. While the self-expandable stent 100 automatically expands after detached from the first through hole 11, the balloon dilatation catheter 1 and the stent release tube 2 are withdrawn to complete the delivery and mounting of the self-expandable stent 100.

What is claimed is:

1. A balloon stent mounting device, which is configured to mount a self-expandable stent on a lesion site of a blood vessel, wherein the balloon stent mounting device comprises:

a balloon dilatation catheter provided with a first through hole along a length direction, and a threading hole is disposed on a side wall of the balloon dilatation catheter, wherein the balloon dilatation catheter is configured to enable a micro guidewire to enter the first through hole through a distal end of the balloon dilatation catheter and pass through the threading hole;

wherein an expansion part is disposed at the distal end of the balloon dilatation catheter, the self-expandable stent is slidably mounted in the first through hole, and the self-expandable stent is located at the distal end of the balloon dilatation catheter;

a stent release tube, wherein the stent release tube is slidably disposed in the first through hole of the balloon dilatation catheter, and a distal end of the stent release tube abuts against the self-expandable stent; and a stopper assembly, wherein a first handle is disposed at a proximal end of the balloon dilatation catheter, a second handle is disposed at a proximal end of the stent release tube, and the stopper assembly is provided with two card slots spaced apart, wherein a cavity is disposed between the two card slots, the stopper assembly is detachably mounted on the first handle and the second handle via the two card slots, a part of a side wall of the stent release tube is located in the cavity, and a distance between the two card slots is no less than a length of the self-expandable stent, and wherein the stopper assembly comprises two stopper blocks that can be spliced.

2. The balloon stent mounting device of claim 1, an inlet is disposed at the proximal end of the balloon dilatation catheter, an outlet is disposed at the distal end of the balloon dilatation catheter, and the stent release tube is configured to penetrate the first through hole of the balloon dilatation catheter through the inlet of the balloon dilatation catheter.

3. The balloon stent mounting device of claim 1, wherein the stent release tube is provided with a second through hole along the length direction, and the side wall of the stent release tube is provided with an avoidance notch matching a position of the threading hole, and a length of the avoidance notch is greater than the length of the self-expandable stent to ensure that the avoidance notch is configured to avoid the micro guidewire in a process of pushing out the self-expandable stent by the stent release tube.

4. The balloon stent mounting device of claim 3, wherein a first guide wall is flexibly disposed on a side of the threading hole away from the self-expandable stent, and the first guide wall is configured to be pressed against the side wall of the stent release tube and provide guidance for the micro guidewire.

5. The balloon stent mounting device of claim 1, wherein side walls of each of the two stopper blocks are respectively provided with grooves, one of the grooves on one of the two stopper blocks is opposite to another of the grooves on another of the two stopper blocks, and in a situation where the two stopper blocks are spliced, the grooves opposite each other are configured to be spliced to form the two card slots and the cavity.

6. The balloon stent mounting device of claim 1, wherein the side wall of the balloon dilatation catheter comprises an inner wall and an outer wall, a fluid channel is disposed between the inner wall and the outer wall, the expansion part is an expansion membrane connected to the outer wall, a proximal end of the fluid channel is connected to a fluid source, and a distal end of the fluid channel is configured to communicate with the expansion membrane.

7. The balloon stent mounting device of claim 1, wherein a developing ring or a developing winding is mounted at the distal end of the balloon dilatation catheter, and a developing ring or a developing winding is mounted on an outside of the self-expandable stent.

8. A stent mounting method using a balloon stent mounting device, wherein the balloon stent mounting device is configured to mount a self-expandable stent on a lesion site of a blood vessel, and the balloon stent mounting device comprises:

a balloon dilatation catheter provided with a first through hole along a length direction, and a threading hole is disposed on a side wall of the balloon dilatation catheter, wherein the balloon dilatation catheter is configured to enable a micro guidewire to enter the first through hole through a distal end of the balloon dilatation catheter and pass through the threading hole;

wherein an expansion part is disposed at the distal end of the balloon dilatation catheter, the self-expandable stent is slidably mounted in the first through hole, and the self-expandable stent is located at the distal end of the balloon dilatation catheter; and a stent release tube, wherein the stent release tube is slidably disposed in the first through hole of the balloon dilatation catheter, and a distal end of the stent release tube abuts against the self-expandable stent;

wherein the balloon stent mounting device further comprises a stopper assembly, wherein a first handle is disposed at a proximal end of the balloon dilatation catheter, a second handle is disposed at a proximal end of the stent release tube, and the stopper assembly is provided with two card slots spaced apart, wherein a cavity is disposed between the two card slots, the stopper assembly is detachably mounted on the first handle and the second handle via the two card slots, a part of a side wall of the stent release tube is located in the cavity, and a distance between the two card slots is no less than a length of the self-expandable stent, and wherein the stopper assembly comprises two stopper blocks that can be spliced; and the stent mounting method comprises the following steps:

mounting the self-expandable stent in a compressed configuration to the distal end of the balloon dilatation catheter, and mounting the stent release tube in the first through hole;

operating the micro guidewire to enter the first through hole through the distal end of the balloon dilatation catheter and to pass through the threading hole;

enabling the balloon dilatation catheter to cooperate with the micro guidewire to push the expansion part of the balloon dilatation catheter to the lesion site;

expanding the expansion part to stretch out the lesion site;

contracting the expansion part, and withdrawing the balloon dilatation catheter until the stent release tube pushes the self-expandable stent out of the first through hole; and withdrawing simultaneously the balloon dilatation catheter and the stent release tube.

9. The stent mounting method of claim 8, an inlet is disposed at the proximal end of the balloon dilatation catheter, an outlet is disposed at the distal end of the balloon dilatation catheter, and the stent release tube is configured to penetrate the first through hole of the balloon dilatation catheter through the inlet of the balloon dilatation catheter.

10. The stent mounting method of claim 8, wherein the stent release tube is provided with a second through hole along the length direction, and the side wall of the stent release tube is provided with an avoidance notch matching a position of the threading hole, and a length of the avoidance notch is greater than the length of the self-expandable stent to ensure that the avoidance notch is configured to avoid the micro guidewire during the pushing out of the self-expandable stent by the stent release tube.

11. The stent mounting method of claim 10, wherein a first guide wall is flexibly disposed on a side of the threading hole away from the self-expandable stent, and the first guide wall is configured to be pressed against the side wall of the stent release tube and provide guidance for the micro guidewire.

12. The balloon stent mounting device of claim 1, wherein side walls of each of the two stopper blocks are respectively provided with grooves, one of the grooves on one of the two stopper blocks is opposite to another of the grooves on another of the two stopper blocks, and in a situation where the two stopper blocks are spliced, the grooves opposite each other are configured to be spliced to form the two card slots and the cavity.

13. The stent mounting method of claim 8, wherein the side wall of the balloon dilatation catheter comprises an inner wall and an outer wall, a fluid channel is disposed between the inner wall and the outer wall, the expansion part is an expansion membrane connected to the outer wall, a proximal end of the fluid channel is connected to a fluid source, and a distal end of the fluid channel is configured to communicate with the expansion membrane.

14. The stent mounting method of claim 8, wherein a developing ring or a developing winding is mounted at the distal end of the balloon dilatation catheter, and a developing ring or a developing winding is mounted on an outside of the self-expandable stent.

* * * * *